United States Patent [19]
Weisman

[11] Patent Number: 6,135,775
[45] Date of Patent: Oct. 24, 2000

[54] LONGITUDINALLY CENTRALLY CONVERGANT DENTAL POST

[76] Inventor: Bernard Weisman, 225 E. 48th St, New York, N.Y. 10017

[21] Appl. No.: 09/368,030

[22] Filed: Aug. 3, 1999

[51] Int. Cl.⁷ .................................................. A61C 5/08
[52] U.S. Cl. ........................................ 433/220; 433/225
[58] Field of Search ................................ 433/173, 174, 433/175, 201.1, 220, 221, 225

[56] References Cited

U.S. PATENT DOCUMENTS

| | | | |
|---|---|---|---|
| 2,289,785 | 7/1942 | Hutchison, Jr. | 433/225 X |
| 5,051,092 | 9/1991 | Miller | 433/225 |
| 5,066,230 | 11/1991 | Weissman | 433/221 X |
| 5,263,996 | 11/1993 | Filhol | 433/220 X |

*Primary Examiner*—Nicholas D. Lucchesi
*Attorney, Agent, or Firm*—Barry G. Magidoff; Paul J. Sutton

[57] ABSTRACT

The present invention relates to a dental prosthetics and more particularly to an improved support post for securing a dental prosthesis, such as an artificial crown, to the root of a tooth. The invention further relates to a method and a device for strengthening a tooth and root from which the nerve has been removed and specifically to a dental post which provides centering for the forming of a bracing filler to internally reinforce the walls of pulpless roots while providing for the support of an artificial prosthesis. The invention further provides for a secondary reinforcing device surrounding the central dental post and also being capable of following the contours of the tooth root. This secondary strengthening and reinforcing element is a flexibly coiled wire of a generally helicoid shape, which also serves as a matrix for the luting of composite filler.

17 Claims, 7 Drawing Sheets

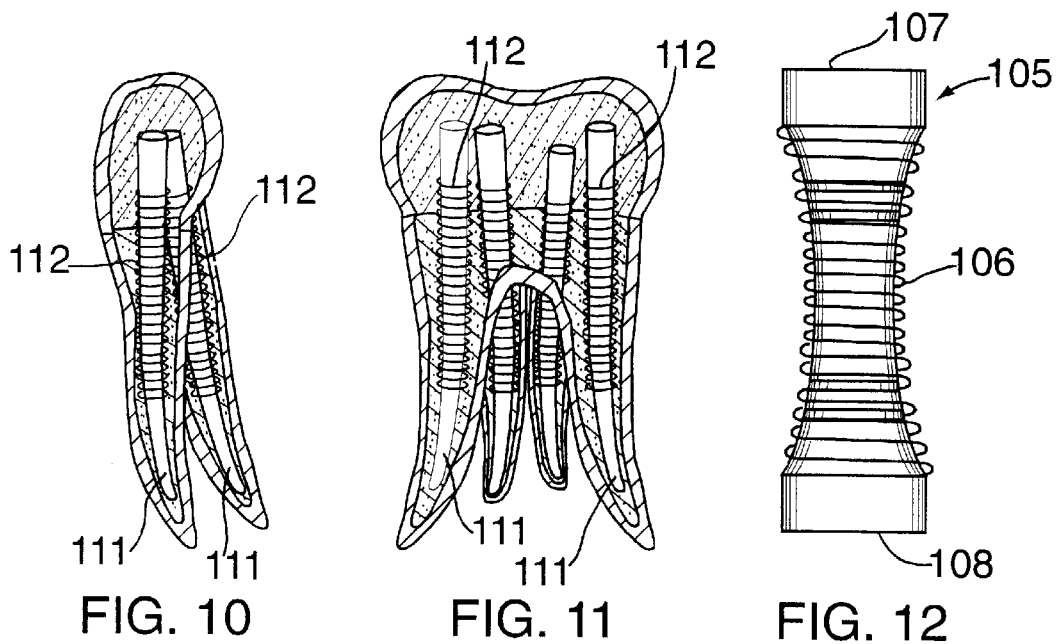
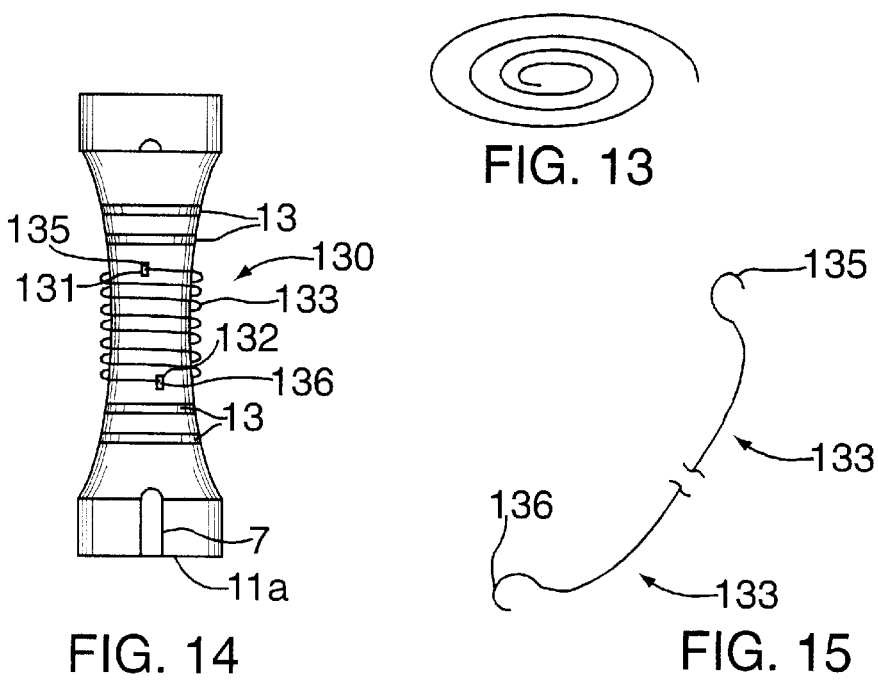

LONGITUDINALLY CENTRALLY CONVERGANT DENTAL POST

The present invention relates to dental prosthetics and more particularly to an improved support post for securing a dental prosthesis, such as an artificial crown, to the root of a tooth. The invention further relates to a method and a device for strengthening a tooth and root from which the nerve has been removed and specifically to a dental post which provides centering for the forming of a bracing filler to internally reinforce the walls of pulpless roots while providing for the support of an artificial prosthesis.

This invention further provides for a secondary reinforcing means surrounding the central dental post and also being capable of following the contours of the tooth root. It is especially significant in those cases where the tooth root is deeply curved and thus requires reinforcing devices that are highly flexible. This secondary strengthening and reinforcing element is a flexibly coiled wire of a generally helicoid shape, which also serves as a matrix for the luting composite filler.

There are a great many shapes used for support posts by the dental art. Similarly, dental posts have been made from a variety of materials including, for example, stainless steel, rigid synthetic polymers, flexible synthetic polymers, opaque materials or light transmitting, translucent or transparent materials.

Previously the configurations of the support posts have varied from a substantially cylindrical shape to having a polygonol cross-section, from having substantially parallel sides, to devices which taper towards the end intended to be most deeply imbedded in the root of the tooth. Support posts have also been formed having somewhat irregular cross-sectional shapes and some of which have a longitudinally centrally divergent shape, such as in U.S. Pat. No. 4,726,770 to Kurer.

The present invention is intended to provide a support post and tooth root reinforcing anchor which insures a secure attachment of a prosthetic coronal replacement, while strengthening the root so as to prevent splitting or cracking of the remaining tooth wall material, while further reinforcing the luting composition retaining the post in place.

According to the present invention, there is provided a tooth reinforcing and prosthetic support anchor post having a central shaft portion, which has a centrally convergent profile, i.e., along its longitudinal axis, and end portions preferably having substantially parallel sides or, alternatively, at least one reverse tapering deep end, intended to be inserted furthest into the root canal of the tooth. The circumferential surface of the centrally convergent shaft portion of the post of this invention is formed in a substantially continuous curve, i.e., a curve without sharp discontinuities, extending in a longitudinal direction parallel to the longitudinal axis of the shaft, and tapers to a central diameter at least 10% narrower than the maximum diameter at each end of the shaft portion.

In a preferred embodiment, the centrally convergent shaft portion of the dental post of this invention is at least 11 millimeters in length, and preferably not greater than 18 millimeters in length; most preferably, the shaft portion has a length of between about 14 and 17 millimeters. The largest diameter at each end of the centrally convergent shaft portion is at least about 0.04 inch in diameter and preferably not more than about 0.07 inch in diameter. The narrowest central section of the post of this invention has a diameter preferably of not less than about 0.02 inch and preferably at least about 0.035 inch, and preferably not greater than about 0.06 inch.

In a most preferred embodiment, the centrally convergent portion is formed integrally with, or intimately connected to, substantially parallel-sided end portions, which each preferably extend at least another 2 millimeters along the longitudinal axis of the post. This permits the user to tailor the overall length of the post, to meet the needs of a particular tooth, without harming the symmetry of the continuously curved centrally convergent shaft portion. Alternatively, at least one of the ends, generally the one extending deepest into the root of the tooth, may be inwardly tapered if that is desired for a particular canal situation. Contrariwise, the end portion intended to directly support the artificial crown, i.e., the end extending outwardly beyond the tooth, may be circumferentially enlarged, relative to the maximum central shaft diameter, if needed to better support the prosthetic crown.

The post can have a substantially circular cross-section, albeit one with a diameter which varies along longitudinal axis of the shaft portion. A shaft portion having a polygonal cross-section, is also within the scope of this invention, if in a particular situation, e.g., it is desired to prevent rotation. Similarly, an oval design will also prevent rotation and avoid the sharp, stress magnifying corners of a polygonol design.

Each end portion can also have a circular cross-section, however, the end portion extending outside of and beyond the tooth canal can most desirably have a polygonal cross-section in order to prevent rotation of the crown and insure a more stable seat for the crown. The precise shape, size and length of the outer end portions, beyond the continuous curve of the centrally converging shaft portion, can be of a variety of shapes or sizes, without affecting the critical shape of the central shaft portion. The end portions can be cut back or otherwise modified, without changing the centrally convergent shaft portion and thus enable ready tailoring for a particular design of e.g., crown or internal root canal.

The dental post of this invention is preferably formed of a rigid material of the type suitable for use in dentistry. In a most preferred embodiment, the material transmits light energy, particularly in the visible and towards the blue end of the spectrum, and includes materials such as a physiologically inert, transparent or optically conductive material, such as a polycarbonate (e.g. Lexan) or other F.D.A.-approved material having the required physical properties for use as a dental support structure. Such a material can provide the needed support as well as permit the transmission of light energy to assist in the curing of the cement material used to hold the post in place within the root canal. Most preferably, the post is also transparent to X-rays, which would permit an unobstructed view of the canal for inspection by the dentist without requiring opening of the canal and removal of the prosthesis and support post. The polymeric transparent material can also be reinforced to increase its strength, as for example by the inclusion of glass or even carbon fibers. In addition to a reinforced polymer resin, a translucent or transparent vitreous material can be used in forming the centrally convergent post. Generally, such vitreous material will be more rigid than even a reinforced polymer resin.

Another aspect of this invention, which may be combined with the centrally convergent dental post, or with dental posts of substantially any other useful shape, is a helicoid flexible wire formed so as to surround the dental post and be as flexible as the dental post if required for steeply curved tooth roots. When the wire and post combination is inserted into the root canal (after the canal has been prepared by generally known dental procedures, such as with a dental reamer),the wire is immersed in the composite luting material used in dentistry, which also holds the post in place; the wire provides a reinforcing matrix for the luting composite, further strengthening the endodontically compromised tooth. The wire forming the coil can have substantially any cross-section. Although generally it is circular in cross-section, the precise shape depends on the method of manufacturing and, for example, if extruded, the cross-section is determine by the shape of the die opening.

The coiled wire can be made of a metallic composition or composites such as reinforced fiberglass rod material or high-density polyesters. The helicoid wire can be utilized together with any type of luting composite, e.g., both self-curing and light curing, known to the dental arts, and which is not antagonistic to the material of the wire or of the dental post. The luting material serves to secure the helicoid wire and the dental post within the root canal walls. The strengthened tooth is better able to withstand the normal forces of normal masticatory function. When the post is formed of a relatively soft resin composition, such as a polycarbonate, or other polymer commonly used in the dental arts, even when it is integrally encased within the luting composite, it can be relatively easily drilled out, to reopen the canal to further work if it becomes necessary; the polymeric post is far more readily drilled out than the composite.

When a steeply curved root is to be strengthened, the dental post and the wire must be extremely flexible. Forming flexible dental posts is well known to the art. Simiilarly, forming flexible coiled wire is well-known, in the wire extrusion art. Moreover, it must be noted that the flexibility of the coiled wire is substantially inherent as a result of its geometry, even when extremely hard, normally rigid metals are used to form the wires. Generally, dental quality stainless steel or titanium metals and alloys can be utilized for the helicoid wire. The wire is preferably not more than about 0.004 inch in diameter and preferably in the range of from about 0.002 to about 0.003 inch in diameter.

The diameter of the helicoid coil is limited by the diameter of a post that would fit the prepared root canal, and is generally in the range of from about 0.04 inch to about 0.07 inch. The diameter of the coil should be sufficient to surround the dental post and to fit within the prepared canal. The coil need not be a snug fit around the post; indeed, a slack fit, or one which permits some movement of the post relative to the coil, may be preferred in order to encapsulate the wire within the luting composite surrounding the post. However, when inserting the coiled wire and post into the root canal, it is preferred that there be a snug fit so that they both pass into the tooth canal together. Thus, it would be most preferred if means were provided tightly securing the coiled wire to the dental post when it is inserted, and then to permit the helicoid wire to expand within the canal to a position intermediate the outer circumference of the dental post and the inner surface of the canal walls.

One procedure would comprise mounting a coil on a dental post, e.g. one of light-transmitting flexible polymer, and inserting the assembled post and wire coil into a canal filled with luting composite. When multiple canals in a multi-rooted molar tooth are thus treated, each root canal can be filled with luting composite and a coil and post can be inserted into each filled root, to form a solid interconnected structure, strengthened to support the coronal replacement. Furthermore, if the post is removable, as with a relatively soft plastic, it can be removed with conventional dental instruments, if retreatment is subsequently required.

The coiled wire of this invention is not limited to use with the centrally convergent dental post of this invention. It can be used with both light transmitting posts, which would be especially useful when working with light-curing luting composites, or with opaque posts, e.g., metallic dental posts, which generally would be used with self-curing luting composites. Metallic posts are especially useful when threaded, especially when the post thread can mate with the coil helix to permit firmly fastening devices to the root, by providing additional traction, or to permit tightening. When both the coil and the threaded post are of metal, the interface will permit threading, removal and rethreading back into the tooth, without quickly wearing out the threads, as happens with threads formed into the luting composite.

Moreover, in some circumstances, the helicoid wire itself can be utilized to transmit light into the medium, e.g., when it is formed of suitable polymeric material; however, such light-transmitting coiled wire materials, from a structural point of view, would not be as desirable as the stronger but non-light-transmitting metals or reinforced polymers, such as fiberglass or carbon fiber wire.

The coiled wire, when formed of a metal, is likely to form a shadow and thus somewhat discolor the appearance of the tooth. This effect can be overcome, or at least reduced, by the well-known means of coating the coiled wire with a thin layer of an opaque material, such as is often used for metal dental posts, and are themselves well known to the art. Such opaque coatings can be formed from colored pigments mixed with a quick-drying alcohol diluent, as is well known in the dental arts.

Further details of the present invention are shown in the accompanying drawings, by way of example and not by way of exclusion. Many portions of the invention, or the context therefore, are shown in schematic representation, where greater detail is unnecessary as the detail will be apparent or otherwise known to those skilled in the art.

Referring to the accompanying drawings:

FIG. 10 is a diagrammatic side elevation view, in cross-section, of a molar tooth, having steeply curved roots, with a dental post and wire coil in each root canal;

FIG. 11 is a front elevation view of the tooth of FIG. 10;

FIG. 12 is a side elevation view of an embodiment of the invention combining the centrally convergent dental post with a substantially cylindrical coil;

FIG. 13 is a bottom plan view of a noncircular convergent helicoid coil of the present invention;

FIG. 14 is a side elevation view of the combination of the centrally convergent dental post with a substantially cylindrical coil, tightly, releasably wound around its shank; and FIG. 15 is an enlarged view of a portion of the coiled wire of the combination of FIG. 14.

Figure 1:
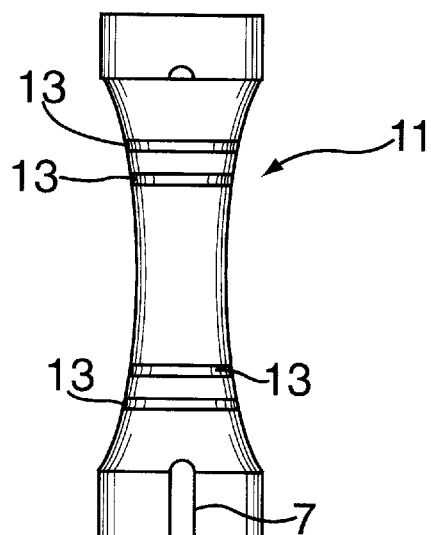
FIG. 1 is an elevation cross-sectional view of a centrally convergent dental post in accordance with the present invention.
Figure 6:
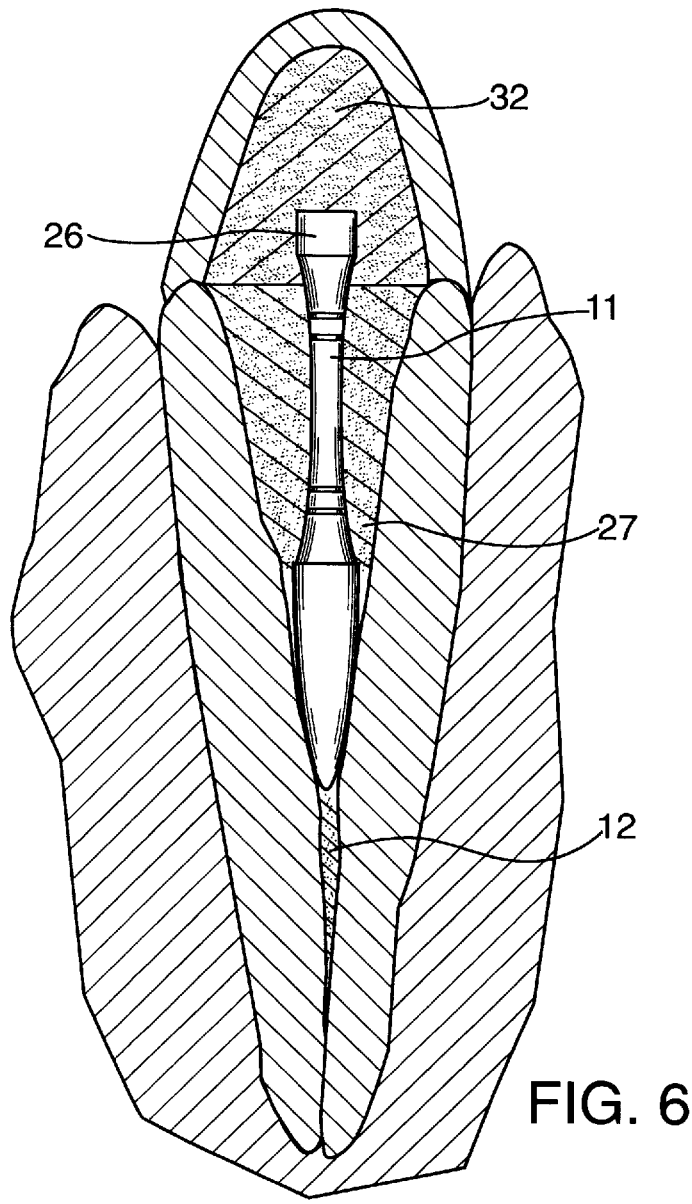
FIG. 6 is an elevation cross-section view of the root of FIG. 5 showing the post of this invention cemented in place and onto which the prosthesis has been mounted.
Figure 2:
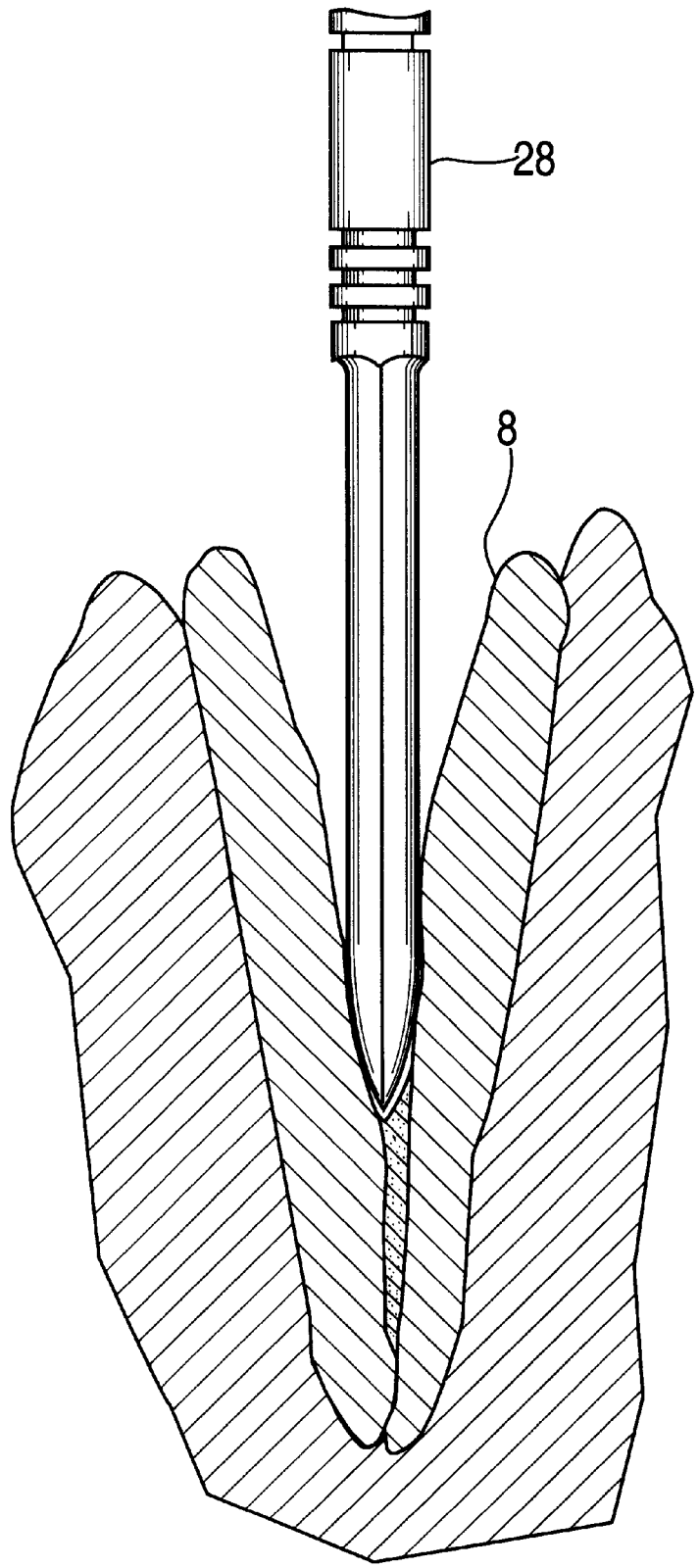
FIG. 2 is an elevation lingual cross-section view of a root being reamed out to remove diseased tooth tissue and thus widen the root canal.
Figure 3:
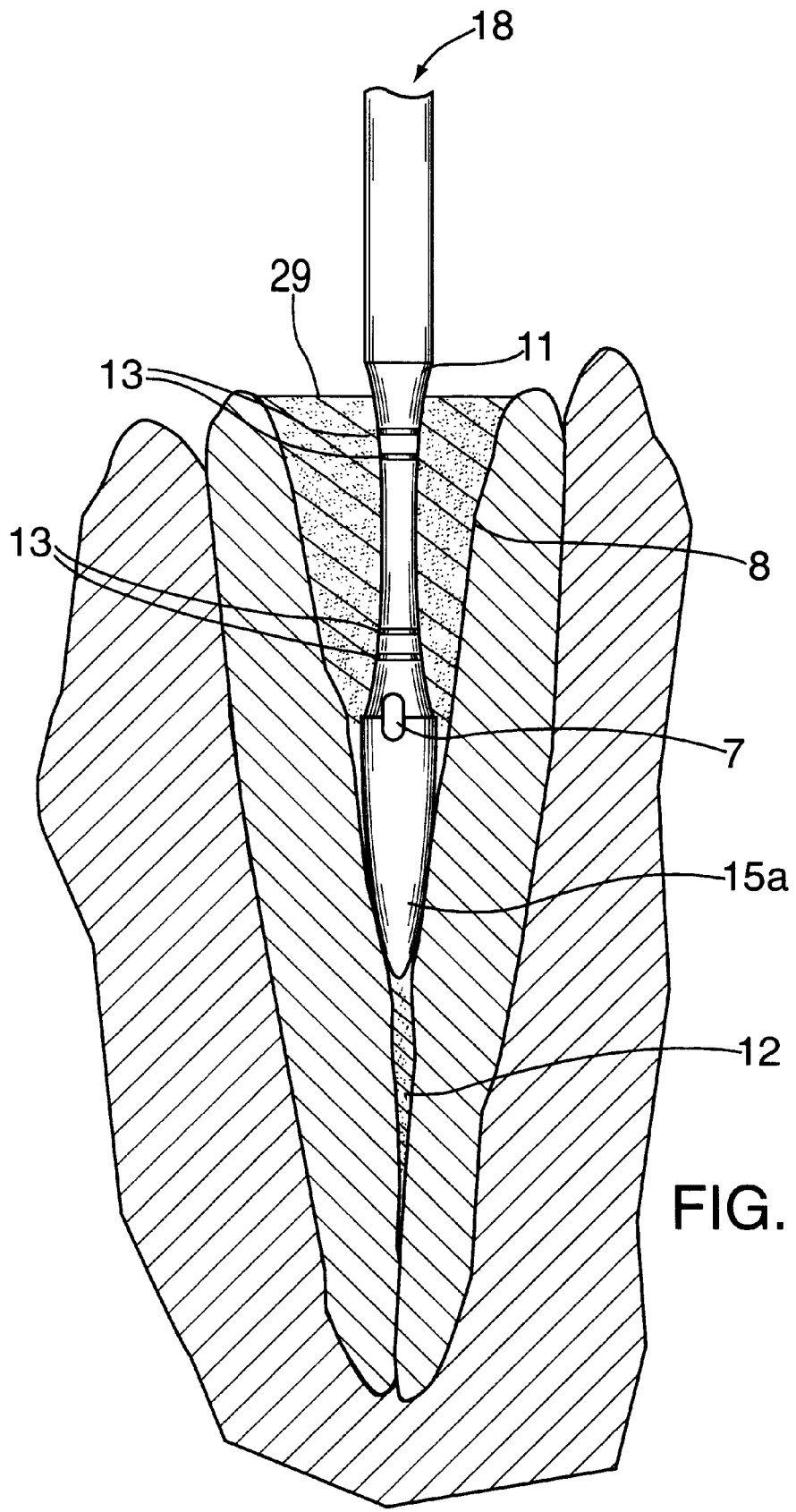
FIG. 3 is an elevation cross-section view showing a reamed out root with a centrally convergent post centered in accordance with this invention, before being cemented in place with composite material.
Figure 4:
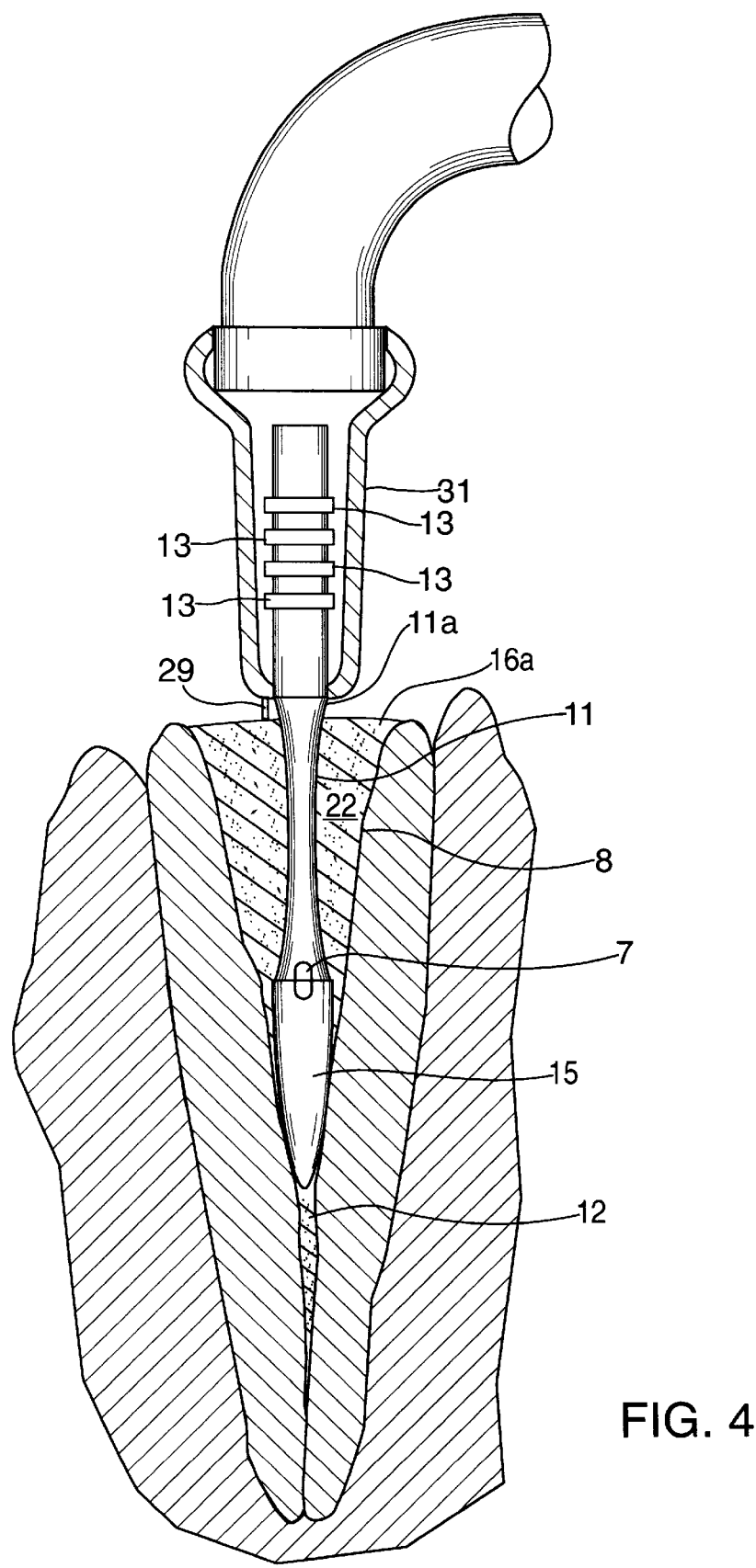
FIG. 4 is an elevation cross-section view of the tooth of FIG. 4 in which the composite material has been placed within the root, surrounding the post, and the tooth is prepared for curing of the filler in accordance with one embodiment of this invention.
Figure 5:
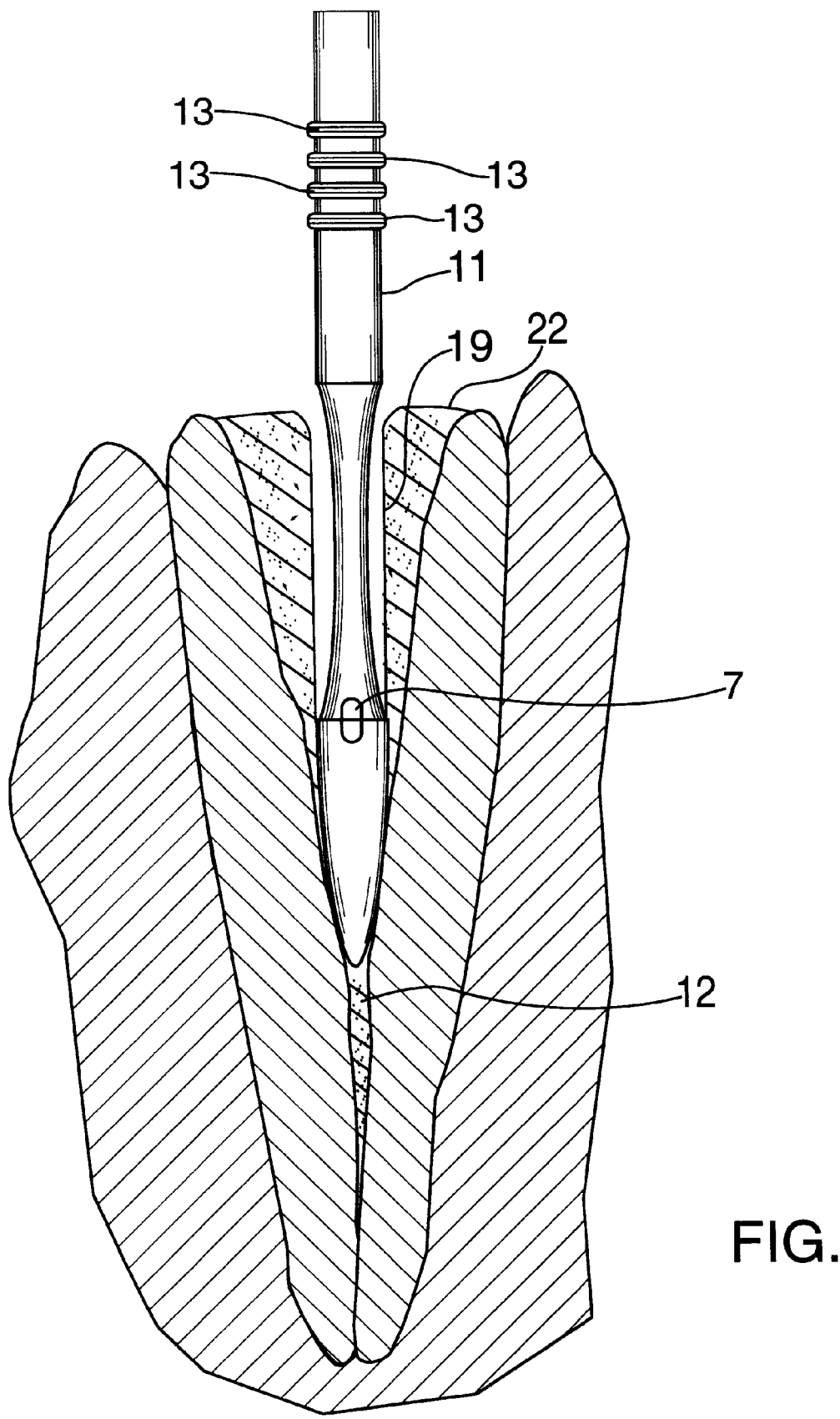
FIG. 5 is an elevation cross-section view of the root of FIG. 4 showing the post of this invention cemented in place before the attachment of the prosthesis.

With reference to the drawings, and in accordance with the present invention, the centrally convergent post of this invention, generally indicated by the numeral 11, can be used in a dental restoration technique to provide for the coronal restoration of a decoronated tooth root 8 as shown in FIG. 2. As is shown in FIG. 2, the canal within the root 8 is cleaned, obturated and contoured, using standard dental instruments—in this case a dental reamer 28. As shown, it is unnecessary to form a smooth circular cross-section opening in the tooth root, as irregular edges or even undercuts will aid in retention of the ultimate prosthetic crown.

In a further preferred embodiment, in order to further enhance the retention of the centrally convergent post in the root canal, the post can be provided with grooves or ribs 13 on the circumference of the post to provide better contact with the surrounding composite material as it cures. The anchoring ribs or grooves 13 may have an incline relative to the longitudinal axis of the post and can be rounded off.

Longitudinally extending grooves 7 can extend along at least one end portion of the post of this invention in order to permit the passage of cement either into the root (if cement is added after the post is in place) or out from the root canal (if the post is inserted into a cement-filled canal). Specifically, the longitudinal grooves 7 are preferably formed in at least one end, i.e., the end which extends deepest into the root canal, so as to permit the passage of luting composite and thus prevent the formation of air spaces. The longitudinal grooves 7 continue from the inner end of the post 11 a to the beginning of the convergent portion to thus relieve any pressure as the post of this invention is inserted into a cement-filled root canal.

The root canal is preferably reamed so that at least at the bottom portion there is a fairly close fit between the end portion 11 a of the post and the side of the canal. Preferably, there is a sufficient annular space for at least a thin layer of the composite to cure between the widest portion of the post 11 and the root canal wall.

After the root canal has been suitably prepared as explained above, the bottom of the canal is sealed by means of a known root filler 12, such as gutta percha. The remaining portion of the canal is then filled with cement or composite 22, so as to surround the circumference of the post 11 within the root canal. Conventional buildup material 19 is subsequently applied around the head-end portion 26 as a reinforcing member and a tooth crown may then be mounted on this material in accordance with conventional means well-known to the art.

The luting composite material can be cured by a variety of methods, including the use of a mixture containing a dual or auto-curing agent, which will cure, within a short period of time after being mixed, and placed within the canal. Most preferably, the composite material is light-curable, as described above, and thus can be cured by the passage of light of the desired frequency, through the light-transmitting tool post 11. When an auto-curing cement is used, the post need not be light-conducting. The concentrated light emitted along the full length of the post 11 is sufficiently intense to hasten the curing of even the innermost portion of the light-curable cement.

In a most preferred embodiment, the luting composite material works together with a nonrigid tool post 11 to provide sufficient resilience to absorb stress on the tooth and root during function and thus reduce the possibility of further strain on the tooth, resisting the frequently encountered split roots. Suitable composite material formulated to act as a somewhat resilient, impact shock absorber, would maintain long-term usefullness for otherwise healthy, embedded roots in the supporting bone structure. Examples of such resilient luting composite material, include the presently commonly used materials, but with higher than usual proportions of filler particles.

To further improve the resilience of the composite, there can also be provided a reinforcing mesh 21 wrapped around the post 11, which becomes embedded in the luting composite. The mesh can be formed of, e.g., a fluorocarbonate polymer, such as Teflon, or a rust-free metal, such as stainless steel or the usual gold or silver alloy compositions to provide the best functionality.

The structurally stronger post 26 is preferably made of a metal acceptable for such use. The outer end of the post 26 extending beyond the tooth is clipped off to the proper length and shaped so that a core material can be attached as a foundation of the coronal restoration 32.

The dental posts of this invention should be of the usual size useful for dentistry. For example, the maximum post diameters should be no greater than about 0.08 inch, and preferably in the range of from about 0.04 to about 0.07 inch. Although the posts can be substantially circular in cross-section, if it is desired that they cannot rotate within the canal, the posts can be formed with an oval cross-section, or with a polygonal cross-section. The length of the posts should preferably be no greater than about 20 millimeters, and are preferably in the range of from about 8 to about 15 millimeters. The length of the inner end portion is preferably not greater than about 3 millimeters, and preferably at least about 0.1 millimeter.

In accordance with the second aspect of the present invention, a helicoid coil of flexible wire material is formed around a dental post. The dental post can be one having a converging end generally towards the bottom of the post or it can be the centrally convergent post described hereinabove. The terms "bottom", "top", "inner" or "outer" respectively are used herein in a relative sense to denote a location relative to the tooth canal. The portion of the post intended to be nearest the crown of the tooth is the 'top' or 'outer' end and the portion of the post nearest the gum or jaw bone is the 'bottom' or 'inner' end of the tooth.

Figure 7:
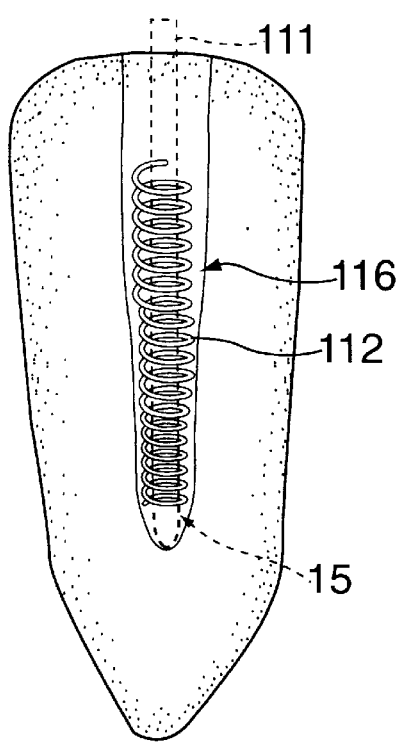
FIG. 7 is an elevation lingual x-ray view of a healthy obturated tooth reinforced using one embodiment of a terminally convergent, transparent post surrounded by a helicoid metal wire coil in accordance with the present invention.

Referring to the drawings, FIG. 7 shows an optically transparent bottom convergent post 111 surrounded by a bottom converging helicoid coil 112, reinforcing a substantially healthy obturated tooth. The post 111 comprises a generally cylindrical shank 113 having a lower bullet-shaped end portion 15 which has a profile substantially matching that of the reamed out bottom of the canal. The coil 112 axially decreases in diameter towards the bottom of the post As shown in FIG. 7, the convergent post 11 is inserted into the reamed canal 8, such that coil 112 surrounding the converging bullet-shaped end 15 fits in the bottom portion of the tooth canal 8, immediately above and in contact with the gutta percha 21 plug, used in the generally accepted manner.

A curable filling material 116, or luting composite, is placed into the open tooth canal 8, and the post 111 and wire coil 112 are then pressed into the luting composite in the canal to the desired depth. In one preferred example, the post can be formed of dental quality stainless steel, and has a diameter at the top of 0.05 inch and at the bottom a diameter of only 0.004 inch. The length of the post is about 11 mm. The wire is also stainless steel, with a diameter of 0.002 inch, formed into a downwardly convergent helical coil 112, which is maintained coaxial with the post 111, maintaining a diameter of about 20% greater than the diameter of the post at the same axial location, i.e., the diameter of the coil varies from about 0.09 inch at the top, to about 0.005 inch at the bottom.

The pitch of the helicoid coil is to be determined by the use to which the coil is to be put, its material of construction, and its size. It is understood that as the pitch increases, the flexibility of the coil decreases; further, if the coil is to serve as a female thread for a threaded post, the pitch is to be determined by the pitch of the post thread. If the tooth canal is steeply curved, it is thus necessary to set the coil pitch and the flexibility of the wire from which the coil is formed to obtain the desired flexibility. For example, in a straight tooth canal the post can be formed of a substantially rigid metal, and the helicoid coil need not be flexible, whereas when a steeply curved tooth root is to be treated, for example the root shown in FIGS. 10 and 11, the helicoid coil should be flexible.

Thus if great flexibility is required, as for example for the highly curved canals of the tooth of FIGS. 10 and 11, materials, such as well-known polymeric materials, or metals such as nickel-titanium ("Ni Ti") alloys, can be utilized.

Referring to FIG. 12, the centrally convergent post 105 of the present invention is shown surrounded by a substantially cylindrical coil 106. Thus, in accordance with this invention, the coil is only loosely formed around the central portion of the post 105 and more closely fit around the substantially cylindrical ends 107,108.

FIG. 13 shows a non circular helicoid coil having an essentially oblong, or elliptical, appearance in cross-section or in plan view, as shown. The coil as shown in FIG. 13 could fit around either a post having an oval cross section, but preferably is used about a post having a circular cross section such that the coil would fit closely about the post at the ends of one diameter but have greater play at other parts of the circumference of the post. It is believed that this provides more effective reinforcement for the luting composite, especially in those root canals having a non circular section.

It is equally within the scope of this invention to utilize a post having a polygonal cross section, such as a square, pentagon or octagon. In addition, the wire itself can have a polygonal cross section where desired.

The coating which can be used on the wire, to avoid the visual shadow which causes discoloration when viewing the tooth, is well known to the art and includes materials such as pigments dispersed in alcohol dispersant, which evaporates rapidly in air.

In one preferred embodiment, the coil is tightly wound about the dental post when the post is inserted into the curable luting composite in the root canal. Thereafter, and before the cement is cured, the coil is released and allowed to expand away from the post and into the luting composite, while remaining substantially concentric with the axis of the post. This can be simply accomplished, for example, by tightly winding the wire coil about the central shank portion of the post, and hooking the ends of the coiled wire into niches formed in the outer surface of the post. At least one of the ends should be readily unhooked from its respective niche, so as to permit the coil 133 to expand in diameter, while remaining substantially concentric to the post 130.

Referring to FIG. 14, the tightly coiled wire 133 is removably secured, as by hooks 135,136, respectively, formed at both ends of the wire 133, to niches 131,132, respectively, formed in the central shank portion of the dental post 130. After the combination of the tight coil and post is in place in the tooth canal, the hooked ends 135,136 can be pushed out of the niches 131,132 and the coil will expand around the post. Simple hooks 135,136, formed by bending the ends of the wire 133, as shown enlarged, in FIG. 15.

Figure 8:
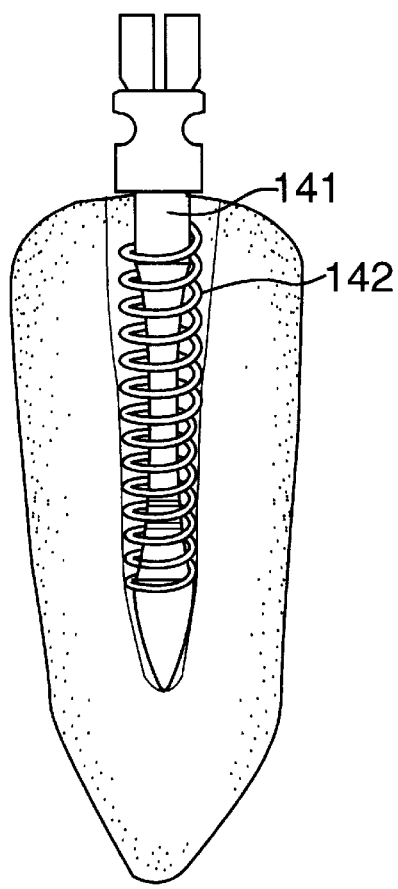
FIG. 8 is an elevation lingual x-ray view of a healthy obturated tooth reinforced using another embodiment of a terminally convergent, threaded metal post surrounded by a helicoid metal wire coil in accordance with the present invention.

Referring to FIG. 8 this can be initially formed using a polymeric post such as in FIG. 7; after the plastic post is removed, the metal post 141 can be screwed into the tooth root, mating with the metal wire coil 142, forming a strong and adjustable connection. The coil 142 can be formed of a suitable dental stainless steel, or nickel-titanium alloy.

Figure 9:
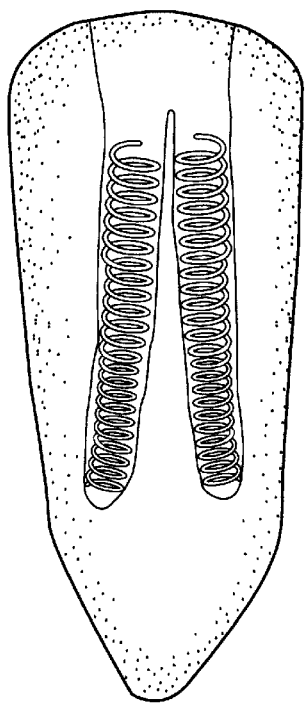
FIG. 9 is a side elevation x-ray view, in cross-section, of a bicuspid molar tooth, with a dental post and wire coil in each root canal.

As shown in FIG. 9, coils and posts can be placed in bicuspid teeth, as shown in this figure, wherein the root is often steeply curved, as in FIGS. 10 and 11. The further advantage of the metal coil is that it is opaque to x-rays, and thus serves to outline the canal, even when the post is of an x-ray transparent polymer. Thus, when it is necessary to remove the plastic post, the metal coil frames its location and that of the canal, for the dentist.

The embodiments of the present invention herein described are presented merely as examples of the present invention. Other embodiments coming within the scope of the present invention will readily subject themselves to those skilled in the art, and shall be deemed to come within the scope of the appended claims.

The patentable embodiments of the invention which are claimed are as follows:

1. A dental tool post for reinforcing an obturated tooth and root, the dental post comprising a central shank portion and a first and a second end portion extending longitudinally respectively of the central portion and concentric to the same axis; the central shank portion being centrally convergent, the circumferential surface of which forming a continuous curve along a longitudinal direction, and reaching a maximum effective diameter at the junctions between the central shank portion and the first-end portion and the second end portion, respectively; at least one of the end portions having a maximum diameter not greater than the maximum diameter of the shank portion; and the post being formed of a physiologically inert material.

2. The dental post of claim 1 wherein the second end portion is substantially cylindrical in shape and has an end surface substantially perpendicular to the longitudinal access of the post.

3. The dental tool post of claim 1 wherein the first end portion tapers to a minimum end diameter.

4. The dental tool post of claim 1 wherein post is formed of a material which is also optically transmitting.

5. The dental post of claim 1 wherein the post has a total length of not more than 21 millimeters and a minimum diameter of not less than 0.02 inch; the length of the first and second end portions being not less than 1 millimeter each.

6. The dental post of claim 1 wherein the physiologically inert material is an optically opaque material selected from the group consisting of metals, vitreous materials and synthetic resinous materials.

7. The dental post of claim 1 wherein the physiologically inert material is selected from the group consisting of optically transmitting synthetic resinous polymers and vitreous materials.

8. A method of reinforcing an obturated tooth and root canal and supporting a dental prosthesis, the method comprising preparing said canal suitably for insertion of a post; sealing the apical portion of the canal with a physiologically suitable, soft resilient material; embedding within a curable composite resin a suitable dental post; curing the composite resin such that a portion of the post extends above the obturated tooth; the dental post comprising a longitudinally extending member comprising a central shank portion and a first end portion and a second end portion; the first end portion being embedded within the tooth canal and at least a portion of the shank portion being embedded within the tooth canal with the second end portion extending beyond the obturated tooth; the central shank portion being formed as a centrally convergent longitudinal member along the longitudinal axis, the circumferential surface of the central shank portion forming a continuous curve longitudinally; and attaching an artificial crown around and over said second end portion atop said obturated tooth.

9. A dental apparatus for reinforcing an obturated tooth and root, the apparatus comprising the combination of a dental post comprising a central shank portion and a first and a second end portions, and a wire formed in a helicoid coil surrounding the dental post at least along the central shank portion.

10. The dental apparatus of claim 9 wherein the wire is secured to the dental post at least at one portion, such that the combination can be inserted into a reamed out root canal as an integral unit.

11. The dental apparatus of claim 9 wherein the dental post is terminally convergent towards the second end and wherein the helicoid coil converges in the same direction as the dental post.

12. The dental apparatus of claim 9 wherein the helicoid coil has a noncircular cross section.

13. The dental apparatus of claim 12 wherein the cross section of the helicoid coil is an ellipsoid.

14. The dental apparatus of claim 9 wherein the helicoid coil has a circular cross section.

15. A method of reinforcing an obturated tooth and root canal and supporting a dental prosthesis, the method comprising preparing said canal suitably for insertion of a post; sealing the apical portion of the canal with a physiologically suitable, soft resilient material; substantially filling the canal with a curable luting composite, embedding within the curable luting composite a suitable dental post combined with a helical wire coil; curing the composite resin such that a portion of the post and the wire coil is embedded in and reinforces the luting composite.

16. The method of claim 15, wherein the wire is removably secured about the dental post so as to be tightly coiled about a central portion of the post, and wherein the wire is released from the post after the combination is inserted into the curable luting composite and before the curable luting composite is cured.

17. The method of claim 15, wherein the wire forming the helicoid coil is of a dental quality metal, and wherein the dental post is formed of a polymeric resin; the method further comprising removing the polymeric resin dental post, and replacing with a dental post formed of a metal and comprising a shank portion having male threads and a head portion extending outwardly beyond the luting composite; the male threads of the metal post being so formed and sized as to mate with the coiled wire in the tooth canal.

* * * * *

UNITED STATES PATENT AND TRADEMARK OFFICE
CERTIFICATE OF CORRECTION

PATENT NO. : 6,135,775
DATED : October 24, 2000
INVENTOR(S) : Bernard Weisman

It is certified that error appears in the above-identified patent and that said Letters Patent is hereby corrected as shown below:

<u>Title page,</u>
Item [54], Title, replace "CONVERGANT" with -- CONVERGENT --
Item [75], Inventors, replace "Bernard Weisman" with -- Bernard Weissman --

Signed and Sealed this

Sixth Day of July, 2004

JON W. DUDAS
*Acting Director of the United States Patent and Trademark Office*